(12) United States Patent
Lang et al.

(10) Patent No.: US 7,179,830 B2
(45) Date of Patent: Feb. 20, 2007

(54) SUBSTITUTED THIENOIMIDAZOLES USEFUL FOR DISEASE TREATMENT AND PREVENTION

(75) Inventors: Hans-Jochen Lang, Hofheim (DE); Uwe Heinelt, Wiesbaden (DE); Klaus Wirth, Kriftel (DE); Thomas Licher, Bad Soden (DE)

(73) Assignee: Sanofi-aventis Deutschland GmbH, Frankfurt (DE)

( * ) Notice: Subject to any disclaimer, the term of this patent is extended or adjusted under 35 U.S.C. 154(b) by 30 days.

(21) Appl. No.: 10/926,118

(22) Filed: Aug. 25, 2004

(65) Prior Publication Data

US 2005/0075385 A1  Apr. 7, 2005

Related U.S. Application Data

(60) Provisional application No. 60/537,738, filed on Jan. 20, 2004.

(30) Foreign Application Priority Data

Sep. 8, 2003  (DE) ................. 103 41 240

(51) Int. Cl.
A61K 31/4188 (2006.01)
C07D 495/04 (2006.01)
(52) U.S. Cl. .................. 514/388; 548/303.7
(58) Field of Classification Search ........ 548/303.7; 514/388
See application file for complete search history.

(56) References Cited

U.S. PATENT DOCUMENTS

| 3,758,476 A | 9/1973 | Rippel et al. |
| 6,005,010 A | 12/1999 | Schwark |
| 6,686,384 B2 | 2/2004 | Hofmeister |

FOREIGN PATENT DOCUMENTS

| DE | 4034728 | 5/1992 |
| EP | 0483683 | 5/1992 |
| WO | WO 0121582 | 3/2001 |
| WO | WO 0172742 | 10/2001 |
| WO | WO 0179186 | 10/2001 |
| WO | WO 02/46169 | 6/2002 |

OTHER PUBLICATIONS

Golub et al., Science, vol. 286, Oct. 15, 1999, pp. 531-537.*
Karmazyn et al., Current Drug Targets—Cardiovascular & Hematological Disorders, vol. 5, No. 4, Aug. 2005, pp. 323-335.*
U.S. Appl. No. 10/309,352, filed Dec. 4, 2002, Hofmeister.
U.S. Appl. No. 10/448,851, filed May, 30, 2003, Lang.
U.S. Appl. No. 10/770,654, filed Feb. 3, 2004, Heinelt.
U.S. Appl. No. 10/771,185, filed Feb. 3, 2004, Heinelt.
U.S. Appl. No. 10/866,843, filed Jun. 14, 2004, Hofmeister.
U.S. Appl. No. 10/892,994, filed Dec. 20, 2002, Heinelt.
U.S. Appl. No. 10/324,041, filed Dec. 20, 2002, Hofmeister.
U.S. Appl. No. 10/441,124, filed Dec. 4, 2001, Hofmeister.
U.S. Appl. No. 09/734,008, filed Dec. 12, 2000, Heinelt.
Akhter S. et al., Squalamine, A Novel Cationic Steroid, Specifically Inhibits The Brush-Border Na+/H+ Exchanger Isoform NHE3, The American Physiological Society, 276, (Cell Physiology 45), (1999) pp. C136-C144.
Ernsberger Paul et al., Clonidine Binds To Imidazole Binding Sites As Well As alpha2-Adrenoceptors In The Ventorolateral Medulla, European Journal Of Pharmacology, 134, 1, (1987) pp. 1-13.
Fliegel Larry et al., Regulation And Characterization Of The Na+/H+ Exchanger, Biochem, Cell Biology, 76, (1998), pp. 735-741.
Jen T. et al., Amidines And Related Compounds. 6. Studies On Structure-Activity Relationships Of Antihypertensive And Antisecretory Agents Related To Clonidine, Journal of Medicinal Chemistry, 18, 1, (1975), pp. 90-99.
Ma, et al., Expression And Localization Of Na+/H+ Exchangers In Rat Central Nervous System, Neuroscience, (1997), vol. 79. No. 2. pp. 591-603.
Mohsen, et al., The Cyclodesulfurization Of Thio Compounds; VII. A New Facile Synthesis Of Na-Substituted Benzimidazoles, Communication, Jan. 1974, S. 41-42.
Omar A-Moshen M.E. et al., The Cyclodesulfurization Of Thio Compounds; XVL Dicyclohexylcarbodimide As An Efficient Cyclodesulfurizing Agent In The Synthesis Of Heterocyclic Compounds From Various Thio Compounds, Synthesis, 1977, pp. 864-865.
Staab Heinz A. et al., Synthese Von Isothiocyanaten, Justus Liebigs Annalen Der Chemie, 657, (1962) pp. 104-107.
Yu, et al., Functional Properties of the Rat Na/H Exchanger NHE-2 Isoform Expressed in Na/H Exchanger-deficient Chinese Hamster Ovary Cells, J. Biol. Chem.; 268; 34; 1993; pp. 25536-25541.

* cited by examiner

*Primary Examiner*—Laura L. Stockton
(74) *Attorney, Agent, or Firm*—Balaram Gupta

(57) ABSTRACT

Substituted thienoimidazoles with a backbone structure of formula I or II:

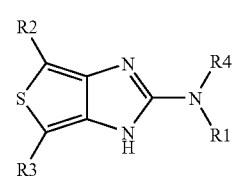

I

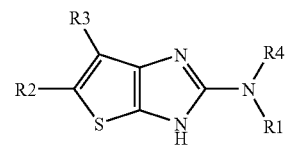

II

These substituted thienoimidazoles are useful in prevention or treatment of various disorders, including respiratory disorders.

13 Claims, No Drawings

SUBSTITUTED THIENOIMIDAZOLES USEFUL FOR DISEASE TREATMENT AND PREVENTION

The invention relates to substituted imidazoles. Medicaments which comprise compounds of this type are useful in the prevention or treatment of various disorders. For instance, some uses of the compounds include the treatment of respiratory disorders and of snoring, and also to improve the respiratory drive, to treat acute and chronic disorders of the kidneys and of the intestines, disorders resulting from ischemic and/or reperfusion events, and resulting from proliferative or fibrotic events, the treatment or prophylaxis of disorders of the central nervous system, of lipid metabolism and of diabetes, of blood coagulation and of infestation by parasites.

The invention relates to compounds of the formula I or II

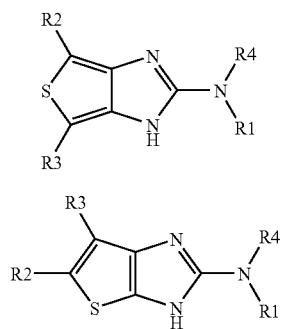

where
R1 is phenyl which is substituted by the radicals R5 and R6 in the 2-and 6-position;
  R5 and R6 are each independently hydrogen, methyl, ethyl, cycloalkyl having 3, 4 or 5 carbon atoms, vinyl, ethynyl, fluorine, chlorine, bromine, iodine, cyano, trifluoromethyl, $SF_5$, methoxy, nitro or —X—R7;
    R7 is alkyl having 1, 2 or 3 carbon atoms, trifluoromethyl or $CH_2$—$CF_3$;
    X is $CH_2$, O, NH or $S(O)_n$;
    n is zero, one or two;
  where R5 and R6 are not both at the same time hydrogen;
or
R1 is 3-thienyl which is substituted by the radicals R5 and R6 in the 2-and 4-position;
  R5 and R6 are each independently hydrogen, methyl, ethyl, cycloalkyl having 3, 4 or 5 carbon atoms, vinyl, ethynyl, fluorine, chlorine, bromine, iodine, CN, $NO_2$, trifluoromethyl, $SF_5$, methoxy or —X—R7;
    R7 is alkyl having 1, 2 or 3 carbon atoms, trifluoromethyl or $CH_2$—$CF_3$;
    X is $CH_2$, O, NH or $S(O)_n$;
    n is zero, one or two;
  where R5 and R6 are not both at the same time hydrogen;
R2 and R3 are each independently hydrogen, fluorine, chlorine, bromine, methyl, CN, OH, —O—$CH_3$, $NO_2$, $NH_2$, —$CF_3$ or —Y—R8;
  R8 is methyl, trifluoromethyl or $CH_2$—$CF_3$;
  Y is $CH_2$, O, NH or $S(O)_m$;
  m is zero, one or two,
R4 is hydrogen, methyl, ethyl, cyclopropyl, cyclopropylmethyl or $CH_2$—$CF_3$;

and their pharmaceutically acceptable salts and their trifluoroacetic acid salts.

Preference is given to compounds of the formula I where
R1 is phenyl which is substituted by the radicals R5 and R6 in the 2-and 6-position;
  R5 and R6 are each independently hydrogen, methyl, ethyl, cycloalkyl having 3, 4 or 5 carbon atoms, vinyl, ethynyl, fluorine, chlorine, bromine, iodine, cyano, trifluoromethyl, $SF_5$, methoxy, nitro or —X—R7;
    R7 is alkyl having 1, 2 or 3 carbon atoms, trifluoromethyl or $CH_2$—$CF_3$;
    X is $CH_2$, O, NH or $S(O)_n$;
    n is zero, one or two;
  where R5 and R6 are not both at the same time hydrogen;
or
R1 is 3-thienyl which is substituted by the radicals R5 and R6 in the 2-and 4-position;
  R5 and R6 are each independently hydrogen, methyl, ethyl, cycloalkyl having 3, 4 or 5 carbon atoms, vinyl, ethynyl, fluorine, chlorine, bromine, iodine, CN, $NO_2$, trifluoromethyl, $SF_5$, methoxy or —X—R7;
    R7 is alkyl having 1, 2 or 3 carbon atoms, trifluoromethyl or $CH_2$—$CF_3$;
    X is $CH_2$, O, NH or $S(O)_n$;
    n is zero, one or two;
  where R5 and R6 are not both at the same time hydrogen;
R2 and R3 are each independently hydrogen, fluorine, chlorine, bromine, methyl, CN, OH, —O—$CH_3$, $NO_2$, $NH_2$, —$CF_3$ or —Y—R8;
  R8 is methyl, trifluoromethyl or $CH_2$—$CF_3$;
  Y is $CH_2$, O, NH or $S(O)_m$;
  m is zero, one or two,
R4 is hydrogen, methyl, ethyl, cyclopropyl, cyclopropylmethyl or $CH_2$—$CF_3$;

and their pharmaceutically acceptable salts and their trifluoroacetic acid salts.

Particular preference is given to compounds of the formula I where
R1 is phenyl which is substituted by the radicals R5 and R6 in the 2-and 6-position;
  R5 and R6 are each independently hydrogen, methyl, ethyl, fluorine, chlorine, bromine or trifluoromethyl;
  where R5 and R6 are not both at the same time hydrogen;
or
R1 is 3-thienyl which is substituted by the radicals R5 and R6 in the 2-and 4-position;
  R5 and R6 are each independently hydrogen, methyl, ethyl, fluorine, chlorine, bromine or trifluoromethyl;
  where R5 and R6 are not both at the same time hydrogen;
R2, R3 and R4 are each hydrogen and their pharmaceutically acceptable salts and their trifluoroacetic acid salts.

One embodiment relates to compounds of the formulae I and II in which R5 and R6 are each independently described by hydrogen, methyl, ethyl, fluorine, chlorine, bromine or trifluoromethyl, but R5 and R6 are not both at the same time hydrogen; preference is given to compounds in which R5 and R6 are each independently described by hydrogen, methyl, fluorine, chlorine or trifluoromethyl, but R5 and R6 are not both at the same time hydrogen. A further embodiment relates to compounds of the formulae I and II in which R5 and R6 are not both described by hydrogen.

A further embodiment relates to compounds of the formulae I and II in which R2 and R3 are each independently described by hydrogen, methyl, ethyl, fluorine, chlorine, bromine or trifluoromethyl; preference is given to compounds in which R2 and R3 are each independently described by hydrogen and methyl; very particular preference is given to compounds in which R2 and R3 are both described by hydrogen.

A further embodiment relates to compounds of the formulae I and II in which R4 is described by hydrogen, methyl or ethyl; preference is given to compounds in which R4 is described by hydrogen.

Especially preferred are compounds of the formula I selected from the group of 2-(4-methyl-3-thienylamino)-1H-thieno[3,4-d]imidazole,
2-(2,6-dichlorophenylamino)-1H-thieno[3,4-d]imidazole,
2-(2-chloro-4-methyl-3-thienylamino)-1H-thieno[3,4-d]imidazole,
2-(2-trifluoromethylphenylamino)-1H-thieno[3,4-d]imidazole,
2-(2,6-dimethylphenylamino)-1H-thieno[3,4-d]imidazole,
2-(2,6-difluorophenylamino)-1H-thieno[3,4-d]imidazole,
2-(2-chloro-6-methylphenylamino)-1H-thieno[3,4-d]imidazole,
2-(2,4-dichloro-3-thienylamino)-1H-thieno[3,4-d]imidazole and
2-(2-chloro-4-methyl-3-thienylamino)-1H-thiano[3,4-d]imidazole, and their pharmaceutically acceptable salts and their trifluoroacetic acid salts.

Particularly especially preferred are compounds of the formula I selected from the group of 2-(2,6-dichlorophenylamino)-1H-thieno[3,4-d]imidazole,
2-(2-chloro-4-methyl-3-thienylamino)-1H-thieno[3,4-d]imidazole and
2-(2,4-dichloro-3-thienylamino)-1H-thieno[3,4-d]imidazole, and their pharmaceutically acceptable salts and their trifluoroacetic acid salts.

When the compounds of the formula I or II contain one or more centers of asymmetry, they may each independently have either S or R configuration. The compounds may be present as optical isomers, as diastereomers, as racemates or as mixtures in any ratios thereof.

The present invention includes all tautomeric forms of the compounds of the formulae I and II.

Compounds of the formulae I and II may bind acid to form salts. Useful acid addition salts are in particular salts of all pharmacologically acceptable acids, for example halides, in particular hydrochlorides, lactates, sulfates, citrates, tartrates, acetates, phosphates, methylsulfonates, p-toluenesulfonates, adipates, fumarates, gluconates, glutamates, glycerol phosphates, benzoates, oxalates, maleates and pamoates, but also trifluoroacetates.

Alkyl radicals may be straight-chain or branched. This also holds when they bear substituents or occur as substituents of other radicals, for example in alkoxy radicals, alkylamino radicals and alkylsulfonyl radicals. Examples of alkyl radicals are methyl, ethyl, n-propyl or isopropyl (=1-methylethyl). Preferred alkyl radicals are methyl or ethyl, more preferably methyl. In alkyl radicals, one or more, for example 1, 2 or 3, hydrogen atoms may be replaced by fluorine atoms. Examples of such fluoroalkyl radicals are trifluoromethyl and 2,2,2-trifluoroethyl. Substituted alkyl radicals may be substituted in any positions.

Examples of cycloalkyl radicals are cyclopropyl, cyclobutyl or cyclopentyl. Substituted cycloalkyl radicals may be substituted in any positions. Cycloalkyl radicals may also occur as substituents of other radicals, for example as cyclopropylmethyl.

The present invention also provides the process, described herein below, for preparing the compounds of the formulae I and/or II.

The present invention relates to a process for preparing a compound of the formulae I or II and/or a pharmaceutically acceptable salt thereof, which comprises a) reacting a diamine of the formulae III or IV with a cyanate of the formula V to give a urea derivative of the formula VI or VII, b) cyclizing the urea derivative of the formula VI or VII to give a compound of the formulae Ia or IIa, and, c) to prepare a compound of the formulae I or II in which R4 is other than hydrogen, derivatizing a compound of the formulae Ia or IIa to give a compound of the formulae I or II

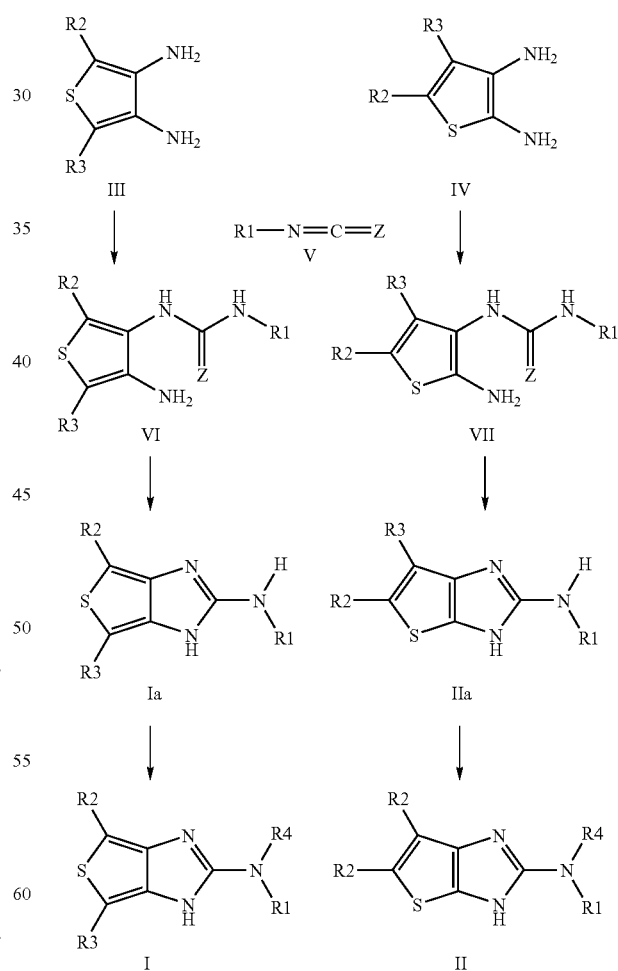

where R1, R2, R3 and R4 are each as defined above, and where Z is oxygen or preferably sulfur.

For instance, substances described by formula I or II can be prepared from isothiocyanates of the formula Va

    Va and the appropriate diamines of the formula III or IV. For this purpose, the diamine of the formula III or IV is initially reacted in an inert solvent, for example an ether such as tetrahydrofuran, with the appropriate isothiocyanate of the formula Va, and operation is effected generally at temperatures of from 0° C. to 100° C., for example at room temperature. The isothiocyanate of the formula Va, if not commercially available, may be prepared from the appropriate anilines by methods known to those skilled in the art, for example by treating with thiophosgene (J. Med. Chem., 1975, 18, 90–99) or thiocarbonyldiimidazole (Justus Liebigs Ann. Chem., 1962, 657, 104). The thiourea derivative formed as an intermediate may be cyclized in a suitable solvent, for example an alcohol such as ethanol, for example by means of methyl iodide (Synthesis, 1974, 41–42) or carbodiimide (Synthesis, 1977, 864–865) at temperatures of from 0° C. to 100° C., for example at the boiling temperature of the solvent or at room temperature, to the corresponding compound of the formula Ia or IIa. A further cyclization method consists in the action of a sulfonyl chloride, for example toluenesulfonyl chloride, on the thiourea derivative formed in an inert solvent, for example an ether such as tetrahydrofuran, at temperatures between 0° C. and 100° C., for example at room temperature, and preference is given to working in the presence of a base, for example NaOH or KOH.

In addition to the above-described isothiocyanates of the formula Va, the isocyanates of the formula Vb

    Vb can also be reacted with diamines of the type of the formula II or III to give compounds of the formula Ia or IIa. In this case, the urea derivative formed as an intermediate is cyclized to the corresponding compounds of the formula Ia or IIa, preferably with phosphorus oxychloride.

The appropriate isocyanates of the formula Vb and the diamines of the formula III or IV are commercially available or can be prepared according to or in analogy to the processes which are described in the literature and are known to those skilled in the art.

For optional derivatization, the compounds of the general formulae Ia or IIa are initially deprotonated with an inorganic base, for example NaH, or an organic base, at a temperature between −30° C. and 100° C., preferably at RT, and then reacted with a suitable electrophile, for example halides such as methyl iodide, at a temperature between −30° C. and 100° C., preferably at RT, to give derivatives of the formulae I or II in which R4 is not hydrogen.

The workup and optionally the purification of the products and/or intermediates are effected by the customary methods such as extraction, chromatography or crystallization and the customary dryings.

In the present invention, it has surprisingly been possible to show that the compounds of the formula I and II constitute potent inhibitors of sodium/proton exchange (NHE), especially of subtype 3 sodium/proton exchanger (NHE3).

The NHE3 inhibitors known hitherto are derived, for example, from compounds of the acylguanidine type (EP825178), norbornylamine types (WO0144164), 2-guanidinoquinazoline type (WO0179186), benzamidine type (WO0121582, WO0172742) or tetrahydroisoquinoline type (WO03048129, WO03055880). The squalamine which has likewise been described as an NHE3 inhibitor (M. Donowitz et al. Am. J. Physiol. 276 (Cell Physiol. 45): C136–C144), according to the current state of knowledge, does not act directly like the compounds of the formula I or II, but rather via an indirect mechanism and thus does not achieve its maximum strength of action until after one hour. Such NHE3 inhibitors having different types of mechanistic action are suitable, for example, as combination partners of the present inventive compounds.

Clonidine, which is distantly related to the inventive compounds, is known to be a weak NHE inhibitor. However, its action on the NHE3 of the rat is extremely moderate at a half-maximum inhibitory concentration ($IC_{50}$) of 620 µM. Instead, it has a certain selectivity for the NHE2 (J. Orlowski et al. J. Biol. Chem. 268, 25536). It should therefore be referred to rather as an NHE2 inhibitor. In addition to the weak NHE action, clonidine has a high affinity for the adrenergic alpha2 receptor and imidazoline I1 receptor, which causes strong blood sugar-lowering action (Ernsberger et al. Eur. J. Pharmacol. 134, 1, 1987).

Compounds which are similar to clonidine but have a thiophene instead of the phenyl ring are disclosed by DE1941761. The structures of the formula I or II described here differ from existing compounds by the fusing of a thieno radical to the imidazole moiety of the formula I or II. This distinction allows the above-described clonidine-like undesired cardiovascular effects mediated by alpha-adrenoreceptor action to be eliminated. At the same time, as a consequence of the substitution differences, the NHE-inhibiting properties of the compounds described here are enhanced down to the micromolar and submicromolar range, while the compounds disclosed by DE1941761 exhibit only very weakly pronounced NHE-inhibiting effects, if any. For instance, the hypotensive described in the application DE1 941761, tiamenidine, in a therapeutically utilizable concentration range, has no relevant inhibitory actions on the NHE subtypes investigated, NHE1, NHE2, NHE3 and NHE5.

The application WO03053434 proposes NHE3 inhibitors of the imidazoline type, the patent application WO 03101984 of the thiophene type and the application DE10304374 of the imidazole type. NHE3 inhibitors of the benzimidazole type are described in WO0246169 and DE10304294. It has been found that, surprisingly, the compounds of the formula I and II described here likewise constitute potent inhibitors of NHE3 and also have advantageous pharmacological and pharmacokinetic properties.

The NHE3 is found in the body of various species, preferentially in the gallbladder, the intestines and in the kidneys (Larry Fliegel et al., Biochem. Cell. Biol. 76: 735–741, 1998), but could also be detected in the brain (E. Ma et al., Neuroscience 79: 591–603).

As a consequence of the NHE-inhibitory properties, the compounds of the formula I and II and their pharmaceutically acceptable salts are suitable for preventing and treating disorders which are caused by activation or by an activated NHE, and also disorders for which NHE-related damage is a secondary cause.

Since NHE inhibitors predominantly act via the influence on the cellular pH regulation, these may favorably be combined with other compounds which likewise regulate the intracellular pH, in which case useful combination partners are inhibitors of the enzyme group of the carbonic anhydrases, inhibitors of bicarbonate ion-transporting systems such as the sodium bicarbonate cotransporter (NBC) or the sodium-dependent chloride-bicarbonate exchanger (NCBE), and also with NHE inhibitors having inhibitory action on other NHE subtypes, because they can amplify or modulate the pharmacologically relevant pH-regulating effects of the NHE inhibitors described here.

The use of the inventive compounds relates to the prevention and the treatment of acute and chronic diseases in veterinary and in human medicine.

A characteristic feature of the pharmacological action of the compounds of the formula I or II is that they lead to an improvement in the respiratory drive. They can therefore be applied to the treatment of disrupted respiratory states, as may occur, for example, in the following clinical states and diseases: disrupted central respiratory drive (for example central sleep apneas, sudden infant death, postoperative hypoxia), muscle-related respiratory disorders, respiratory disorders after long-term ventilation, respiratory disorders in the course of adaptation at altitude, obstructive and mixed type of sleep apneas, acute and chronic pulmonary diseases with hypoxia and hypercapnia.

In addition, the compounds increase the muscle tone of the upper airways, so that snoring is suppressed. The compounds specified therefore advantageously find use to prepare a medicament for preventing and treating sleep apneas and muscle-related respiratory disorders and to prepare a medicament for preventing and treating snoring.

A combination of an NHE inhibitor of the formula I or II with a carbonic anhydrase inhibitor (for example acetazolamide) may be found to be advantageous, the latter inducing metabolic acidosis and thus itself increasing the respiratory activity, so that enhanced action and reduced use of active ingredient can be achieved.

As a consequence of their NHE3-inhibitory action, the inventive compounds protect the cellular energy reserves which are rapidly exhausted in the course of toxic and pathogenic events and thus lead to cell damage or to cell death. The energy-intensive ATP-consuming sodium absorption in the proximal tubule is temporarily shut down under the influence of the NHE3 inhibitors, and the cell can thus survive an acute pathogenic, ischemic or toxic situation. The compounds are therefore suitable, for example, as a medicament for treating ischemic noxae, for example of acute renal failure. In addition, the compounds are also suitable for treating all chronic renal disorders and nephritis forms which lead to chronic renal failure as a consequence of increased protein excretion. Accordingly, the compounds of the formula I or II are suitable for preparing a medicament for treating late diabetic damage, diabetic nephropathy and chronic renal disorders, especially of all renal inflammations (nephritides) which are associated with increased protein/albumin excretion.

It has been found that the compounds used in accordance with the invention have a mild laxative action and accordingly may also be used advantageously as laxatives or in the event of impending constipation.

In addition, the inventive compounds can also be used advantageously for the prevention and therapy of acute and chronic disorders of the intestinal tract, which are caused, for example, by ischemic states in the intestinal region and/or by subsequent reperfusion or by inflammatory states and events. Such complications may be observed, for example, as a result of inadequate bowel peristalsis, as can be observed, for example, frequently after surgical interventions, in the event of constipation or greatly reduced bowel activity.

The inventive compounds provide the possibility of preventing gallstone formation.

The inventive NHE inhibitors are generally suitable for treating diseases which are induced by ischemia and by reperfusion.

Owing to their pharmacological properties, the inventive compounds are suitable as antiarrhythmic medicaments.

Their cardioprotective components makes the NHE inhibitors outstandingly suitable for infarction prophylaxis and infarction treatment, and also for treating angina pectoris, in which case they also preventively inhibit or greatly reduce pathophysiological processes where ischemically induced damage arises, especially on provocation of ischemically induced cardiac arrhythmias. Owing to the protective actions against pathological hypoxic and ischemic situations, the compounds of the formula I or II used in accordance with the invention, as a consequence of inhibition of the cellular $Na^+/H^+$ exchange mechanism, may be used as a medicament for treating all acute or chronic ischemia-induced damage or diseases induced primarily or secondarily thereby.

This also relates to their use as medicaments for surgical interventions. For instance, the inventive compounds may be used in organ transplants, in which case the compounds can be used for the protection of the organs in the donor before and during the removal, and of the removed organs, for example in the course of treatment with or their storage in physiological bath liquids, and in the course of transfer into the recipient organism pretreated with compounds of the formula I or II.

The compounds are likewise valuable medicaments having protective action when performing angioplastic surgical interventions, for example on the heart or else on peripheral organs and vessels.

Since NHE inhibitors protect human tissue and organs effectively not only against damage which is caused by ischemia and reperfusion, but also against the cytotoxic action of medicaments, as find use especially in cancer therapy and the therapy of autoimmune disorders, combined administration with compounds of the formula I or II is suitable for reducing or for suppressing the cytotoxic effects of a therapy. The reduction in cytotoxic effects, especially in cardiotoxicity, as a consequence of comedication with NHE inhibitors, also allows the dose of the cytotoxic therapeutics to be increased and/or medication with such medicaments to be prolonged. The therapeutic benefit of such a cytotoxic therapy may be considerably increased by the combination with NHE inhibitors.

The compounds of the formula I or II are especially suitable for therapy with medicaments which have an undesired cardiotoxic component.

In accordance with their protective action against ischemically induced damage, the inventive compounds are also suitable as a medicament for treating ischemias of the nervous system, especially of the central nervous system, and they are suitable, for example, for treating stroke or cerebral edema.

The compounds of the formula I or II are also suitable for the therapy and prophylaxis of disorders and disruptions which are induced by hyperexcitability of the central nervous system, especially for treating epileptic disorders, centrally induced clonic and tonic spasms, states of psychological depression, anxiety states and psychoses. In these cases, it is possible to employ the inventive NHE inhibitors alone or in combination with other antiepileptic substances or antipsychotic active ingredients, or carbonic anhydrase inhibitors, for example with acetazolamide, and also with further inhibitors of NHE or of the sodium-dependent chloride-bicarbonate exchanger (NCBE).

In addition, the inventive compounds of the formula I or II are likewise suitable for treating types of shock, for example allergic, cardiogenic, hypovolemic and bacterial shock.

The compounds of the formula I or II may likewise be used for preventing and for treating thrombotic disorders, since, as NHE inhibitors, they can also inhibit platelet aggregation itself. In addition, they can inhibit or prevent the excess release, taking place after ischemia and reperfusion, of inflammation and coagulation mediators, especially of von Willebrand factor and of thrombogenic selectin proteins. This allows the pathogenic action of thrombogenic and inflammation-relevant factors to be reduced and eliminated. Therefore, the NHE inhibitors of the present invention can be combined with further anticoagulative and/or thrombolytic active ingredients, for example recombinant or natural tissue plasminogen activator, streptokinase, urokinase, acetylsalicylic acid, thrombin antagonists, factor Xa antagonists, medicaments having fibrinolytic activity, thromboxan receptor antagonists, phosphodiesterase inhibitors, factor VIIa antagonists, clopidogrel, ticlopidine, etc. Combined use of the present NHE inhibitors with NCBE inhibitors and/or with inhibitors of carbonic anhydrase, for example with acetazolamide, is particularly favorable.

In addition, the inventive NHE inhibitors feature strong inhibiting action on the proliferation of cells, for example on fibroblast cell proliferation and on proliferation of smooth vascular muscle cells. Therefore, the compounds of the formula I or II are useful as valuable therapeutic agents for diseases in which cell proliferation constitutes a primary or secondary cause, and can therefore be used as antiatherosclerotic, agents against chronic renal failure, cancers. They can thus also be used for treating organ hypertrophies and hyperplasias, for example of the heart and the prostate. Compounds of the formula I or II are therefore suitable for preventing and for treating heart failure (congestive heart failure=CHF) and also in the treatment and prevention of prostate hyperplasia or prostate hypertrophy.

A further feature of NHE inhibitors is a retardation or prevention of fibrotic disorders. They are thus suitable as an excellent agent for treating fibroses of the heart, and also pulmonary fibrosis, hepatic fibrosis, renal fibrosis and other fibrotic disorders.

Since the NHE is significantly increased in essential hypertensives, the compounds of the formula I or II are suitable for preventing and for treating high blood pressure and cardiovascular disorders. In these cases, they can be used alone or with a suitable combination and formulation partner for the treatment of high blood pressure and cardiovascular disorders. For example, one or more diuretics having a thiazide-like action, loop diuretics, aldosterone and pseudoaldosterone antagonists such as hydrochloro-thiazide, indapamide, polythiazide, furosemide, piretanide, torasemide, bumetanide, amiloride, triamteren, spironolactone or eplerone, may be combined with compounds of the formula I or II. In addition, the NHE inhibitors of the present invention may be used in combination with calcium antagonists such as verapamil, diltiazem, amlodipine or nifedipine, and also with ACE inhibitors, for example ramipril, enalapril, lisinopril, fosinopril or captopril. Further favorable combination partners are also β-blockers such as metoprolol, albuterol, etc., antagonists of the angiotensin receptor and its receptor subtypes such as losartan, irbesartan, valsartan, omapatrilat, gemopatrilat, endothelin antagonists, renin inhibitors, adenosine receptor antagonists, inhibitors and activators of potassium channels such as glibenclamide, glimepiride, diazoxide, cromocalim, minoxidil and their derivatives, activators of the mitochondrial ATP-sensitive potassium channel (mitoK(ATP) channel), inhibitors of further potassium channels such as Kv1.5, etc.

As a consequence of their antiphlogistic action, the inventive NHE inhibitors have may be used as anti-inflammatory drugs. Mechanistically, it is the inhibition of the release of inflammation mediators which is notable. The compounds may thus be used alone or in combination with an antiphlogistic agent in the prevention or treatment of chronic and acute inflammatory disorders. The combination partners used are advantageously steroidal and nonsteroidal anti-inflammatory drugs.

It has also been found that NHE inhibitors exhibit a beneficial influence on the serum lipoproteins. They may therefore be employed for the prophylaxis and for the regression of atherosclerotic lesions because they eliminate a causal risk factor. These include not only the primary hyperlipidemias, but also certain secondary hyperlipidemias, as occur, for example, in diabetes. In addition, NHE inhibitors lead to a distinct reduction in infarctions induced by metabolic abnormalities and especially to a significant reduction in the induced infarction size and its severity.

NHE inhibitors of the formula I or II therefore advantageously find use for the preparation of a medicament for treating hypercholesterolemia; for the preparation of a medicament for preventing atherogenesis; for the preparation of a medicament for preventing and treating atherosclerosis, for the preparation of a medicament for preventing and treating diseases which are induced by increased cholesterol levels, for the preparation of a medicament for preventing and treating diseases; which are induced by endothelial dysfunction, for the preparation of a medicament for preventing and treating atherosclerosis-induced hypertension, for the preparation of a medicament for preventing and treating atherosclerosis-induced thromboses, for the preparation of a medicament for preventing and treating hypercholesterolemia- and endothelial dysfunction-induced ischemic damage and postischemic reperfusion damage, for the preparation of a medicament for preventing and for treating cardiac hypertrophies and cardiomyopathies and congestive heart failure (CHF), for the preparation of a medicament for preventing and treating hypercholesterolemia- and endothelial dysfunction-induced coronary vasospasms and myocardial infarctions, for the preparation of a medicament for treating the conditions mentioned in combination with blood sugar-lowering substances, preferably with angiotensin converting enzyme (ACE) inhibitors and angiotensin receptor antagonists. A combination of an NHE inhibitor of the formula I or II with a blood lipid level-lowering active ingredient, preferably with an HMG-CoA reductase inhibitor (for example lovastatin or pravastatin), in which case the latter induces hypolipidemic action and thus increases the hypolipidemic properties of the NHE inhibitor of the formula I or II, constitutes a favorable combination having enhanced action and reduced use of active ingredient.

For instance, NHE inhibitors lead to effective protection against endothelial damage of varying origins. This protection of the vessels against the syndrome of endothelial dysfunction makes NHE inhibitors valuable medicaments for preventing and for treating coronary vasospasms, peripheral vessel diseases, especially intermittent claudication, atherogenesis and atherosclerosis, left-ventricular hypertrophy and dilated cardiomyopathy, and thrombotic disorders.

NHE inhibitors are also suitable for treating non-insulin-dependent diabetes (NIDDM), in which, for example, insulin resistance is suppressed. To enhance antidiabetic activity and quality of action of the inventive compounds, it may in this case be favorable to combine them with a biguanide such as metformin, with an antidiabetic sulfonylurea such as glyburide, glimepiride, tolbutamide, etc., with a glucosidase inhibitor, with a PPAR agonist such as rosiglitazone, pioglitazone, etc., with an insulin product of different administration form, with a DB4 inhibitor, with an insulin sensitizer or with meglitinide.

In addition to the acute antidiabetic effects, NHE inhibitors counteract the development of diabetic late complications and can therefore be used as medicaments for preventing and treating diabetic late complications such as diabetic nephropathy, diabetic neuropathy, diabetic retinopathy, diabetic cardiomyopathy and other disorders occurring as a consequence of diabetes. In this case, they may advantageously be combined with the antidiabetic medicaments described above under NIDDM treatment. The combination with a favorable administration form of insulin may be particularly significant in this context.

In addition to the protective effects against acute ischemic events and the subsequent equally acutely stressful reperfusion events, NHE inhibitors also exhibit direct therapeutically utilizable actions against diseases and disorders of the entire mammalian organism which are connected to the manifestations of the chronically progressing aging process and which can also occur independently of acute hypoperfusion states and also under normal, nonischemic conditions. These pathological age-related manifestations, induced over the long period of aging, such as illness, invalidity and death, which have recently been made amenable to treatment with NHE inhibitors are diseases and disorders whose essential cause are aging-related changes in vital organs and their function and which become increasingly significant in the aging organism.

Disorders which are connected to functional impairment, to age-related manifestations of wear of organs are, for example, inadequate response and reactivity of the blood vessels to contraction and relaxation reactions. This age-related decrease in vasoreactivity to constrictory and relaxing stimuli, which are an essential process of the cardiovascular system and thus of life and of health, can be significantly eliminated or reduced by NHE inhibitors. An important function and a measure of the maintenance of vaso reactivity is the blockage or retardation of the age-related progressive endothelial dysfunction which can be eliminated highly significantly by NHE inhibitors. NHE inhibitors are thus outstandingly suitable for treating and preventing the age-related progressive endothelial dysfunction, especially of intermittent claudication. NHE inhibitors are also outstandingly suitable for treating and preventing heart failure, congestive heart failure (CHF) and also for treating and especially for preventing age-related forms of cancer. In this case, a useful combination is with hypotensive medicaments, such as with ACE inhibitors, angiotensin receptor antagonists, diuretics, $CA^{+2}$ antagonists, etc., or with metabolism-normalizing medicaments such as hypocholesterolemic agents. The compounds of the formula I or II are thus suitable for preventing age-related tissue changes and for prolonging life while maintaining a high quality of life.

The inventive compounds are effective inhibitors of the cellular sodium-proton antiporter (Na/H exchanger) which is elevated in numerous disorders (essential hypertension, atherosclerosis, diabetes, etc.) also in those cells which are readily amenable to measurements, for example in erythrocytes, thrombocytes or leukocytes. The compounds used in accordance with the invention are therefore suitable as outstanding and simple scientific tools, for example in their use as diagnostic agents for determining and differentiating different forms of hypertension, but also of atherosclerosis, of diabetes and of diabetic late complications, proliferative disorders, etc.

In addition, NHE3 inhibitors are suitable for treating (human and veterinary) disorders induced by bacteria and by protozoa. The diseases induced by protozoa are in particular malarial diseases in humans and coccidiosis in poultry.

The compounds are also suitable as means for controlling sucking parasites in human and veterinary medicine, and also in crop protection. Preference is given in this context to the use as an agent against blood-sucking parasites in human and veterinary medicine.

Also claimed is a curative composition for human, veterinary or phytoprotective use, comprising an effective amount of a compound of the formula I and II and/or a pharmaceutically acceptable salt thereof, together with pharmaceutically acceptable carriers and additives, alone or in combination with other pharmacological active ingredients or medicaments.

Medicaments which comprise a compound of the formula I or II or a pharmaceutically acceptable salt thereof may be administered, for example, orally, parenterally, intramuscularly, intravenously, rectally, nasally, by inhalation, subcutaneously or by a suitable transcutaneous administration form, the preferred administration depending on the particular characteristics of the disorder. The compounds of the formula I or II may be used alone or together with pharmaceutical excipients, both in veterinary and in human medicine, and in crop protection. The medicaments comprise active ingredients of the formula I and II and/or a pharmaceutically acceptable salt thereof generally in an amount of from 0.01 mg to 1 g per dose unit.

Which excipients are suitable for the desired medicament formulation is familiar to those skilled in the art on the basis of their expert knowledge. In addition to solvents, gel formers, suppository bases, tablet excipients and other active ingredient carriers, it is possible to use, for example, antioxidants, dispersants, emulsifiers, antifoams, flavorings, preservatives, solubilizers or dyes.

For an oral administration form, the active compounds are mixed with the additives suitable for this purpose, such as carriers, stabilizers or inert diluents, and are converted to the suitable administration forms by the customary methods such as tablets, coated tablets, hard gelatin capsules, aqueous, alcoholic or oily solutions. Useful inert carriers include, for example, gum arabic, magnesia, magnesium carbonate, potassium phosphate, lactose, glucose or starch, especially corn starch. The formulation may also be effected either as dry granules or as wet granules. Useful oily carriers or solvents are, for example, vegetable or animal oils such as sunflower oil or fish liver oil.

For subcutaneous, percutaneous or intravenous administration, the active compounds used, if desired with the substances customary for this purpose, such as solubilizers, emulsifiers or further excipients, are converted to solution, suspension or emulsion. Useful solvents are, for example, water, physiological saline solution or alcohols, for example ethanol, propanol, glycerol, and additionally also sugar solutions such as glucose or mannitol solutions, or else a mixture of the different solvents mentioned.

Suitable pharmaceutical formulations for the administration in the form of aerosols are, for example, solutions, suspensions or emulsions of the active ingredient of the formula I or II in a pharmaceutically acceptable solvent, in particular ethanol or water, or a mixture of such solvents.

The formulation may, if required, also comprise other pharmaceutical excipients such as surfactants, emulsifiers and stabilizers, and also a propellant gas. Such a formulation typically contains the active ingredient in a concentration of from about 0.1 to 10% by weight, in particular from about 0.3 to 3% by weight.

The dosage of the active ingredient of the formula I or II to be administered and the frequency of administration depends upon the potency and duration of action of the compounds used; additionally also on the nature and severity of the disease to be treated, and also the gender, age, weight and individual responsiveness of the mammal to be treated.

On average, the daily dose of a compound of the formula I or II in the case of a patient weighing about 75 kg is at least 0.001 mg/kg, preferably from 0.1 mg/kg up to at most 30 mg/kg, preferably 1 mg/kg, of body weight. In acute situations, for instance directly after suffering apnetic states at altitude, for instance immediately after suffering apnetic states at altitude, even higher doses may also be necessary. Especially in the case of i.v. administration, for instance in the case of an infarction patient in an intensive care unit, up to 300 mg/kg per day may be required. The daily dose may be divided into one or more, for example up to 4 individual doses.

Experimental Descriptions and Examples:

EXAMPLE 1

2-(4-Methyl-3-thienylamino)-1H-thieno[3,4-d]imidazole hydrochloride

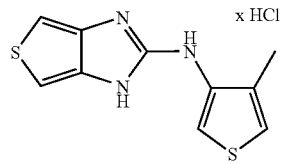

a) N-(3-Amino-4-thienyl)-N'-(4-methyl-3-thienyl) thiourea

A mixture of 1.87 g of 3,4-diaminothiophene dihydrochloride, 60 ml of anhydrous tetrahydrofuran (THF) and 2.58 g of N-ethyl-N,N-diisopropylamine was stirred at room temperature for 30 minutes and then admixed with 1.5 g of 4-methyl-3-thienyl isothiocyanate. After stirring over approx. 18 hours, the solvent was distilled off, the residue admixed with water and extracted repeatedly with ethyl acetate. After the combined organic phases had been treated with activated carbon, they were dried over sodium sulfate and the solvent was once again distilled off. The N-(3-amino-4-thienyl)-N'-(4-methyl-3-thienyl)thiourea was obtained as an amorphous foamy solid.

For further characterization, 0.15 g of N-(3-amino-4-thienyl)-N'-(4-methyl-3-thienyl)thiourea in 20 ml of ethyl acetate was made strongly acidic using a hydrogen chloride gas-saturated ether solution and the solid was filtered off.

Hygroscopic product, decomposition point from 110° C.

b) 2-(4-Methyl-3-thienylamino)-1H-thieno[3,4-d] imidazole hydrochloride 5.05 g of methyl iodide were added to a suspension of 1.2 g of N-(3-amino-4-thienyl)-N'-(4-methyl-3-thienyl)thiourea in 40 ml of anhydrous ethanol and the mixture was boiled under reflux for 5 hours. After the solvent had been distilled off on a Rotavapor, the residue was admixed with water, made alkaline using aqueous saturated sodium hydrogencarbonate solution and extracted repeatedly with ethyl acetate. The combined organic phases were dried over sodium sulfate and treated with activated carbon, and the solvent was distilled off on a Rotavapor. The residue was then purified by column chromatography on silica gel using a mixture of 10 parts by volume of dichloromethane and 1 part by volume of methanol, and, after again distilling off the solvent, crystallized under diisopropyl ether. Brown solid, decomposition point 105° C.

EXAMPLE 2

2-(2,6-Dichlorophenylamino)-1H-thieno[3,4-d]imidazole hydrochloride

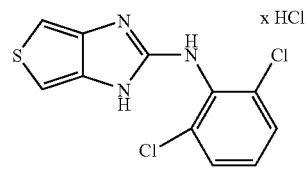

a) N-(3-Amino-4-thienyl)-N'-(2,6-dichlorophenyl) thiourea

A mixture of 1.87 g of 3,4-diaminothiophene dihydrochloride, 60 ml of anhydrous THF and 2.58 g of N-ethyl-N,N-diisopropylamine was stirred at room temperature for 30 minutes and then admixed with 2.04 g of 2,6-dichlorophenyl isothiocyanate. After the mixture had been heated to 40° C. for 10 minutes, it was stirred at room temperature for approx. 18 hours, and the solvent was distilled off, and the residue admixed with water and extracted repeatedly with ethyl acetate. After the combined organic phases had been treated with activated carbon, they were dried over sodium sulfate and the solvent was again distilled off. A crystalline solid was obtained and, after stirring with a little ethyl acetate, was filtered off. M.p. 165° C.

b) 2-(2,6-Dichlorophenylamino)-1H-thieno[3,4-d] imidazole hydrochloride 2.5 g of methyl iodide were added to a suspension of 0.951 g of N-(3-amino-4-thienyl)-N'-(2,6-dichlorophenyl) thiourea in 40 ml of anhydrous ethanol and the mixture was boiled on a reflux condenser for 6 hours. After the solvent had been distilled off on a Rotavapor, the residue was admixed with water, made alkaline using an aqueous saturated sodium hydrogencarbonate solution and extracted repeatedly with ethyl acetate. The combined organic phases were dried over sodium sulfate and treated with activated carbon, and the solvent was distilled off on a Rotavapor. The residue was then purified by column chromatography on silica gel using a mixture of 10 parts by volume of dichloromethane and 1 part by volume of methanol. After the solvent had been distilled off, a brown oily-amorphous product was obtained. It was dissolved in a little ethyl acetate, made strongly acidic using a hydrogen chloride gas-saturated ether solution, and, after adding a little acetone, boiled until complete crystallization. M.p. >300° C.

EXAMPLE 3

2-(2,6-Dichlorophenylamino)-4,6-dimethyl-1H-thieno[3,4-d]imidazole hydrochloride

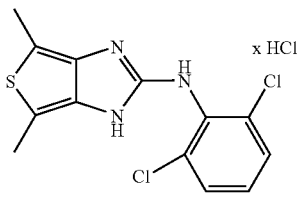

a) N-(3-Amino-2,5-dimethyl-4-thienyl)-N'-(2,6-dichlorophenyl)thiourea

A mixture of 0.5 g of 3,4-diamino-2,5-dimethylthiophene dihydrochloride, 30 ml of anhydrous THF and 0.49 g of triethylamine was stirred at room temperature for 30 minutes and then admixed with 0.569 g of 2,6-dichlorophenyl isothiocyanate. After the mixture had been heated to 40° C. for 30 minutes, it was stirred at room temperature for approx. 18 hours, the solvent was distilled off, the residue admixed with water and the precipitate filtered off and purified by column chromatography on silica gel using a mixture consisting of equal parts by volume of toluene and ethyl acetate. After the solvent had been distilled off, a foamy, amorphous product of m.p. 143–148° C. was obtained which, after melting, solidified again with a new m.p. of >300° C.

b) 2-(2,6-Dichlorophenylamino)-4,6-dimethyl-1H-thieno[3,4-d]imidazole hydrochloride 0.664 g of methyl iodide was added to a solution of 0.27 g of N-(3-amino-2,5-dimethyl-4-thienyl)-N'-(2,6-dichlorophenyl)thiourea in 30 ml of anhydrous ethanol and the mixture was boiled under reflux conditions for approx. 10 hours. After the solvent had been distilled off on a Rotavapor, the residue was admixed with water and extracted repeatedly with ethyl acetate. The combined organic phases were dried over sodium sulfate and the solvent was distilled off on a Rotavapor. The residue was then purified by column chromatography on silica gel using a mixture of 20 parts by volume of ethyl acetate, 10 parts by volume of n-heptane, 3 parts by volume of glacial acetic acid. After the solvent had been distilled off, the residue was dissolved in a little ethyl acetate, made strongly acidic using a hydrogen chloride gas-saturated diethyl ether solution, and the amorphous precipitate was fully crystallized by heating. M.p. 270–273° C.

EXAMPLE 4

2-(4-Methyl-3-thienylamino)-4,6-dimethyl-1H-thieno[3,4-d]-imidazole hydrochloride

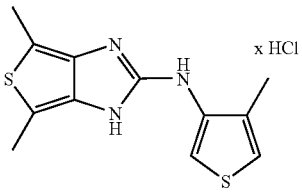

a) N-(3-Amino-2,5-dimethyl-4-thienyl)-N'-(4-methyl-3-thienyl)thiourea

A mixture of 1 g of 3,4-diamino-2,5-dimethylthiophene dihydrochloride, 60 ml of anhydrous THF and 1.05 g of triethylamine was stirred at room temperature for 30 minutes and then admixed with 0.902 g of 4-methyl-3-thienyl isothiocyanate. After the mixture had been heated to 35–40° C. for 15 minutes, it was stirred for approx. 18 hours, the solvent was distilled off and the residue was admixed with water and extracted repeatedly with ethyl acetate. After the solvent of the combined organic phases had been distilled off, the residue was purified by column chromatography on silica gel using a solvent mixture of equal parts of toluene and ethyl acetate. After the solvent had been distilled off under reduced pressure, a semicrystalline oil was obtained and was used without further purification.

b) 2-(4-Methyl-3-thienylamino)-4,6-dimethyl-1H-thieno[3,4-d]imidazole hydrochloride 0.97 g of methyl iodide was added to a suspension of 0.34 g of N-(3-amino-2,5-dimethyl-4-thienyl)-N'-(4-methyl-3-thienyl)thiourea in 40 ml of anhydrous ethanol, and the mixture was boiled under reflux for 6 hours. After the solvent had been distilled off on a Rotavapor, the residue was admixed with water, made alkaline using an aqueous saturated sodium hydrogencarbonate solution and extracted repeatedly with ethyl acetate. The combined organic phases were dried over sodium sulfate and treated with activated carbon, and the solvent was distilled off on a Rotavapor. The residue was then purified by column chromatography on silica gel using a mixture of 20 parts by volume of ethyl acetate and 10 parts by volume of n-heptane and 3 parts by volume of glacial acetic acid. After the solvent had been distilled off, trituration under diisopropyl ether afforded a brown crystalline product. m.p. 159–164° C.

The product was dissolved in a little ethyl acetate, made strongly acidic with a hydrogen chloride gas-saturated diethyl ether solution and heated to precipitate the brownish-colored, crystalline end product. M.p. 230–232° C.

EXAMPLE 5

2-(2-Chloro-4-methyl-3-thienylamino)-1H-thieno[3,4-d]imidazole hydrochloride

a) 4-Methyl-3-trifluoroacetylaminothiophene 609 mg (=0.83 ml) of triethylamine and, after stirring for 10 minutes, 464 mg (=0.307 ml) of trifluoroacetic anhydride were added to a suspension of 300 mg of 3-amino-4-methylthiophene in 20 ml of anhydrous THF. Once the exothermic reaction had abated, the mixture was stirred at room temperature for a further 2 hours and left to stand overnight. After the solvent had been distilled off, the oily residue was dissolved in ethyl acetate, the organic phase was washed once with water and once with dilute hydrochloric acid and once again with water, the organic phase was dried over sodium sulfate and the solvent was distilled off.

The 4-methyl-3-trifluoroacetylaminothiophene which was obtained as a dark oily-amorphous product was used for the next stage without further purification.

b) 2-Chloro-4-methyl-3-trifluoroacetylaminothiophene

A solution of 3.2 g of N-chlorosuccinimide in 50 ml of glacial acetic acid was added dropwise to a mixture of 5 g of 4-methyl-3-trifluoroacetylaminothiophene in 70 ml of glacial acetic acid, and the mixture was then stirred at room temperature for 30 minutes and at 50° C. for a further hour. The solvent was distilled off, and the residue was admixed with water and adjusted to pH 10 using 2N NaOH. The mixture was extracted using ethyl acetate, and the organic phase was washed with water and dried over sodium sulfate. After the solvent had been distilled off, a dark-colored oily product was obtained and was chromatographically purified on silica gel using an elution mixture of 10 parts by volume of toluene and 2 parts by volume of n-heptane. After the solvent had been distilled off, the product was obtained as a light yellow-colored oil.

c) 3-Amino-2-chloro-4-methylthiophene hydrochloride 400 mg of 2-chloro-4-methyl-3-trifluoroacetylaminothiophene were admixed with 1.5 ml of hydrazine hydrate and then stirred at 50° C. for one hour. The mixture was admixed with water, the solution was extracted using ethyl acetate and the organic phase was washed once with dilute acetic acid and once more with water. After the organic phase had been dried over sodium sulfate, it was made strongly acidic using hydrogen chloride-saturated diethyl ether, and the solvent was distilled off on a Rotavapor under reduced pressure. After distilling off to a substantial extent, the mixture was admixed again with ethyl acetate and the solvent was again distilled off, in the course of which brown-colored crystals separated out. The solid was filtered off rapidly and transferred to a desiccator for drying over diphosphorus pentoxide.

Brown-colored, crystalline, hygroscopic solid. Sublimation point: 120° C.

d) 2-Chloro-4-methyl-3-thienyl isothiocyanate

A mixture prepared from 0.5 g of 3-amino-2-chloro-4-methylthiophene hydrochloride, 8 ml of methylene chloride and 0.2 ml of water was added dropwise within 15 minutes to a mixture prepared from a solution of 0.57 g of sodium hydrogen carbonate in 6 ml of water, 20 ml of methylene chloride and 0.34 g of thiophosgene. The mixture was stirred at room temperature for 30 minutes, the organic phase was then removed and the aqueous phase was extracted once more with methylene chloride. The combined organic phases were washed once more with water and dried over sodium sulfate, and the solvent was distilled off. Owing to its sensitivity, the isothiocyanate obtained in this way as a dark oil was used for the further reactions without further purification.

e) N-(4-Amino-3-thienyl)-N'-(2-chloro-4-methyl-3-thienyl)thiourea 0.55 g of 3,4-diaminothiophene dihydrobromide was added to a solution of 0.51 g of N-ethyl-N,N-diisopropylamine in 30 ml of anhydrous THF, the mixture was stirred at room temperature for approx. 5 minutes and the solution was then admixed with a mixture of 0.4 g of 2-chloro-4-methyl-3-thienyl isothiocyanate in 5 ml of THF. The mixture was stirred at room temperature for 3 hours and at 40° C. for 10 minutes. After it had been left to stand overnight, the solvent was distilled off, and the residue was treated with water and extracted with ethyl acetate. The insoluble fraction was filtered off, and the organic phase was washed with water and dried over sodium sulfate. After the solvent had been distilled off, the product was purified by column chromatography on silica gel using a mixture of 1 part by volume of toluene and 1 part by volume of ethyl acetate and, after the solvent had been distilled off, the N-(4-amino-3-thienyl)-N'-(2-chloro-4-methylthienyl)thiourea was obtained as a crystalline solid.

M.p.: 132–135° C.

f) 2-(2-Chloro-4-methyl-3-thienylamino)-1H-thieno[3,4-d]imidazole hydrochloride A solution of 108.4 mg of p-toluenesulfonyl chloride in 5 ml of anhydrous THF was added dropwise to a mixture prepared from a solution of 157 mg of N-(4-amino-3-thienyl)-N'-(2-chloro-4-methylthienyl)thiourea in 15 ml of THF and a solution of 51.08 mg of NaOH in 2 ml of water. The resulting dark solution was stirred at room temperature for 2 hours, the solvent was distilled off and the residue was admixed with water. After extraction with ethyl acetate, the organic phase was washed with water and dried over sodium sulfate. After the solvent had been distilled off, the residue was purified by column chromatography on silica gel using a mixture of 20 parts by volume of ethyl acetate, 10 parts by volume of n-heptane, 3 parts by volume of glacial acetic acid as the eluent, which was then distilled off under reduced pressure. A viscous amorphous product was obtained and was dissolved in ethyl acetate and made strongly acidic using hydrogen chloride gas-saturated diethyl ether. The crystallization of the amorphous hydrochloric acid salt which separated out was brought about by scratching. M.p.: >300° C.

EXAMPLE 6

2-(2-Trifluoromethylphenylamino)-1H-thieno[3,4-d]imidazole hydrochloride

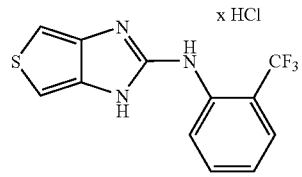

a) N-(3-Amino-4-thienyl)-N'-(2-trifluoromethylphenyl)thiourea 0.8 g of 3,4-diaminothiophene dihydrobromide was added to a mixture of 0.74 g of N-ethyl-N,N-diisopropylamine in 40 ml of anhydrous THF, and the mixture was stirred at room temperature for 10 minutes, and then admixed with 0.58 g of 2-trifluoromethylphenyl isothiocyanate. The mixture was stirred at room temperature for 3 hours and at 40° C. for a further 10 minutes, and left to stand at room temperature overnight. After the solvent had been distilled off, the residue was admixed with water and extracted with ethyl acetate, and the insoluble fraction was filtered off. The organic phase was washed with water and dried over sodium sulfate, the solvent was distilled off and the residue was purified by column chromatography on silica gel using a mixture of 1 part by volume of toluene and 1 part by volume of ethyl acetate.

Crystalline solid of m.p. 122–128° C.

b) 2-(2-Trifluoromethylphenylamino)-1H-thieno[3,4-d]imidazole hydrochloride A solution of 165.3 mg of p-toluenesulfonyl chloride in 5 ml of THF was added dropwise to a mixture prepared from a solution of 250 mg of N-(3-amino-4-thienyl)-N'-(2-trifluoromethylphenyl)thiourea in 15 ml of THF and a solution of 77.8 mg of NaOH in 3 ml of water. After stirring at room temperature for 2 hours, the solvent was distilled off, and the residue was admixed with water and extracted with ethyl acetate. After the washing, the organic phase was dried over sodium sulfate, the solvent was distilled off and the residue was purified by column chromatography on silica gel using a mixture of 20 parts by volume of ethyl acetate, 10 parts by volume of n-heptane and 3 parts by volume of glacial acetic acid. After the solvent of the fraction which had been identified by the LC-MS technique had been distilled off, the residue was dissolved in a little ethyl acetate, made strongly acidic using a solution of hydrogen chloride gas in diethyl ether, and the crystals were filtered off after having been left to stand overnight.

Crystalline solid, m.p. 194–196° C.

EXAMPLE 7

2-(2,6-Dimethylphenylamino)-1H-thieno[3,4-d]imidazole hydrochloride

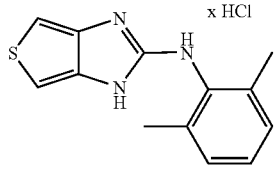

a) N-(3-Amino-4-thienyl)-N'-(2,6-dimethylphenyl)thiourea was obtained in a similar manner to the method specified in Example 6a) by reacting a mixture prepared from 0.74 g of N-ethyl-N,N-diisopropylamine in 40 ml of THF, 0.8 g of 3,4-diaminothiophene dihydrobromide and 0.47 g of 2,6-dimethylphenyl isothiocyanate.

Crystalline solid. M.p. 188–191° C.

b) 2-(2,6-Dimethylphenylamino)-1H-thieno[3,4-d]imidazole hydrochloride was obtained in a similar manner to the method specified in Example 6b from 380 mg of N-(3-amino-4-thienyl)-N'-(2,6-dimethylphenyl)thiourea, 135.4 mg of NaOH and 287.3 mg of p-toluenesulfonyl chloride. Crystalline substance. M.p. >310° C.

EXAMPLE 8

2-(2,6-Difluorophenylamino)-1H-thieno[3,4-d]imidazole hydrochloride

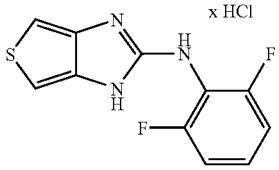

a) N-(3-Amino-4-thienyl)-N'-(2,6-difluorophenyl)thiourea was obtained in a similar manner to the method specified in Example 6a) by reacting a mixture prepared from 0.74 g (=1.01 ml) of N-ethyl-N,N-diisopropylamine in 40 ml of THF, 0.8 g of 3,4-diaminothiophene dihydrobromide and 0.496 g of 2,6-dimethylphenyl isothiocyanate.

Crystalline solid. M.p. 135–140° C.

b) 2-(2,6-Difluorophenylamino)-1H-thieno[3,4-d]imidazole hydrochloride was obtained in a similar manner to the method specified in Example 6b from 335 mg of N-(3-amino-4-thienyl)-N'-(2,6-dimethylphenyl)thiourea, 81.36 mg of NaOH and 172.7 mg of p-toluenesulfonyl chloride. Crystalline substance. M.p. 296° C.

EXAMPLE 9

2-(2-Chloro-6-methylphenylamino)-1H-thieno[3,4-d]imidazole hydrochloride

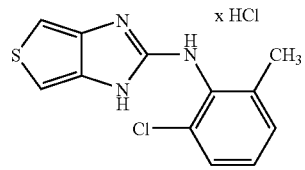

a) N-(3-Amino-4-thienyl)-N'-(2-chloro-6-methylphenyl)thiourea was obtained in a similar manner to the method specified in Example 6a) by reacting a mixture prepared from 0.74 g (=1.01 ml) of N-ethyl-N,N-diisopropylamine in 40 ml of THF, 0.8 g of 3,4-diaminothiophene dihydrobromide and 0.473 g of 2-chloro-6-methylphenyl isothiocyanate.

Crystalline solid. M.p. 168–170° C.

b) 2-(2-Chloro-6-methylphenyl)-1H-thieno[3,4-d]imidazole hydrochloride was obtained in a similar manner to the method specified in Example 6b from 170 mg of N-(3-amino-4-thienyl)-N'-(2-chloro-6-methylphenyl)thiourea, 56.4 mg of NaOH and 119.7 mg of p-toluenesulfonyl chloride. Crystalline substance. M.p. >310° C.

EXAMPLE 10

2-(2,4-Dichloro-3-thienylamino)-1H-thieno[3,4-d]imidazole hydrochloride

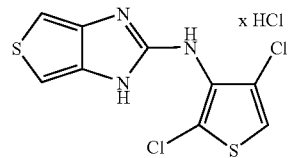

a) Methyl 3-acetylaminothiophene-2-carboxylate was obtained by reacting 471 g of methyl 3-aminothiophene-2-carboxylate with 226.64 ml of acetic anhydride in 500 ml of toluene. Colorless crystalline product. M.p. 94–95° C.

b) Methyl 3-acetylamino-4,5-dichlorothiophene-2-carboxylate was obtained by reacting 19.9 g of methyl 3-acetylaminothiophene-2-carboxylate in 100 ml of chloroform with 17.9 ml of sulfuryl chloride ($SO_2Cl_2$) in 120 ml of chloroform by stirring at 40° C. for 2 hours and subsequently boiling under reflux conditions for 15 minutes. After the solvent had been distilled off, the residue was crystallized in ethyl acetate.

Crystalline solid. M.p. 136–138° C.

c) Methyl 3-acetylamino-4-chlorothiophene-2-carboxylate was obtained by catalytically hydrogenating a mixture of 25 g of methyl 3-acetylamino-4,5-dichlorothiophene-2-carboxylate in 300 ml of methanol, 9.5 g of triethylamine and with 10 g of palladium on carbon and room temperature and 760 mmHg column (standard pressure conditions). After the calculated amount of hydrogen had been absorbed, the catalyst was filtered off, the solvent was distilled off on a Rotavapor and the product was crystallized under water.

Colorless crystalline substance. M.p. 143–147° C.

d) Methyl 3-amino-4-chlorothiophene-2-carboxylate was obtained by stirring a solution of 7 g of methyl 3-acetylamino-4-chlorothiophene-2-carboxylate in a mixture of 50 ml of methanol and 50 ml of concentrated hydrochloric acid at 60° C. for 4 hours and at room temperature for 2 days. The mixture was filtered, the solvent was distilled to about ⅓ of the starting volume, approx. 100 ml of water were added and the crystals were filtered off after stirring at room temperature. Crystalline product. M.p. 62–64° C.

e) 3-Amino-4-chlorothiophene was obtained by heating 19.9 g of methyl 3-amino-4-chlorothiophene-2-carboxylate in a solution of 16.4 g of potassium hydroxide in 150 ml of water under reflux conditions for 90 minutes. The mixture was cooled to 60° C. and approx. 170 ml of aqueous 2N HCl were cautiously added dropwise with stirring and while maintaining the temperature, in the course of which vigorous foaming took place as a consequence of decarboxylation. The mixture was stirred for a further 30 minutes and cooled, the brown precipitate was filtered off, and the filtrate was adjusted to pH 11–12 using NaOH and extracted 3–4 times with methylene chloride. The combined organic phases were washed with water and dried over sodium sulfate, and, after the solvent had been distilled off, a brown oil was obtained and was used without further purification and was stored under argon as a protective gas.

f) 4-Chloro-3-trifluoroacetylaminothiophene was obtained by adding 2.29 g of trifluoroacetic anhydride to a solution of 2 g of 3-amino-4-chlorothiophene and 4.54 g of triethylamine in 40 ml of anhydrous THF.

Exothermic reaction. The mixture was then stirred at room temperature for 3 hours, the solvent was distilled off, and the residue was admixed with water and extracted with ethyl acetate. After the organic phase had been washed with water and subsequently dried over sodium sulfate, the solvent was distilled off. The desired product was obtained as an oily material and was further processed without further purification.

g) 2,4-Dichloro-3-trifluoroacetylaminothiophene

A solution of 1.4 g of N-chlorosuccinimide in 25 ml of glacial acetic acid was added dropwise with stirring to a solution of 2.3 g of 4-chloro-3-trifluoroacetylaminothiophene in 60 ml of glacial acetic acid, the mixture was stirred at 40–45° C. for a further 35 minutes and the solvent was distilled off. The residue was admixed with water and extracted with ethyl acetate, the organic phase was washed with water and dried over sodium sulfate, and the solvent was distilled off. The residue was purified by column chromatography on silica gel using a mixture of 10 parts by volume of toluene and 2 parts by volume of n-heptane, and removed from the still unconverted monochloro compound.

Crystalline compound. M.p. 56–58° C.

h) 3-Amino-2,4-dichlorothiophene

A mixture of 0.26 g of 2,4-dichloro-3-trifluoroacetylaminothiophene and 2.0 ml of 80% hydrazine hydrate solution was stirred at 50° C. for 1 hour and, after having been left to stand overnight at room temperature, admixed with water. The mixture was extracted with ethyl acetate and washed with water, the organic phase was dried over sodium sulfate and the solvent was distilled off. Crystalline solid. M.p.: 50–52° C.

i) 2,4-Dichloro-3-thienyl isothiocyanate

A solution of 0.66 g of 3-amino-2,4-dichlorothiophene in 15 ml of methylene chloride was added dropwise over the course of 15 minutes to a mixture of 8 ml of methylene chloride, 0.825 g of sodium hydrogen carbonate dissolved in 6 ml of water and 0.496 g of thiophosgene. After stirring at room temperature over 2–3 hours, the organic phase was removed and the aqueous phase was extracted twice more with methylene chloride. The combined organic phases were washed with water and dried over sodium sulfate, and the solvent was distilled off. The isothiocyanate was obtained as a dark-colored product and, owing to its sensitivity, was reacted further without purifying operations.

j) N-(4-Amino-3-thienyl)-N'-(2,4-dichloro-3-thienyl)thiourea was obtained in a similar manner to the method described in Example 5e by reacting 0.84 g of 3,4-diaminothiophene dihydrobromide with 0.8 g of 2,4-dichloro-3-thienyl isothiocyanate and 0.49 g of N-ethyl-N,N-diisopropylamine in THF. Crystalline product. M.p. 110–115° C.

k) 2-(2,4-Dichloro-3-thienylamino)-1H-thieno[3,4-d]imidazole hydrochloride

A solution of 108.4 mg of p-toluenesulfonyl chloride in 5 ml of anhydrous THF was added dropwise to a mixture prepared from a solution of 157 mg of N-(4-amino-3-thienyl)-N'-(2,4-dichlorothienyl)thiourea in 15 ml of THF and a solution of 51.08 mg of NaOH in 2 ml of water. The resulting dark solution was stirred at room temperature for 2 hours, the solvent was distilled off and the residue was admixed with water. After extraction with ethyl acetate, the organic phase was washed with water and dried over sodium sulfate. After the solvent had been distilled off, the residue was purified by column chromatography on silica gel using a mixture of 20 parts by volume of ethyl acetate, 10 parts by volume of n-heptane, 3 parts by volume of glacial acetic acid as an eluent, which was then distilled off under reduced pressure. A viscous amorphous product was obtained which was dissolved in ethyl acetate and made strongly acidic using hydrogen chloride gas-saturated diethyl ether. The crystallization of the amorphous hydrochloric acid salt was brought about by scratching. M.p.: >300° C.

EXAMPLE 11

2-(2-chloro-4-methyl-3-thienylamino)-1H-thieno[3,4-d]imidazole

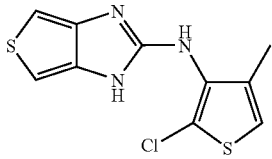

is obtained by adding saturated sodium hydrogencarbonate solution to a suspension of 306 mg of 2-(2-chloro-4-methyl-3-thienylamino)-1H-thieno[3,4-d]imidazole hydrochloride (example 5) in 40 ml of water, in the course of which a pH of 10 is established. After the suspension had been stirred at room temperature for 1 hour, the solid was filtered off and washed repeatedly with water, and the product was dried in an air stream. Colorless crystalline product, decomposition point from 180° C.

Pharmacological Data:

Determination of the NHE Inhibition

Test Description:

This test determined the recovery of the intracellular pH ($pH_i$) after acidification, and this recovery occurs in the case of functional NHE even under bicarbonate-free conditions. To this end, the $pH_i$ was determined using the pH-sensitive fluorescent dye BCECF (Calbiochem, the BCECF-AM precursor is used). The cells were initially loaded with BCECF. The BCECF fluorescence was determined in a Ratio Fluorescence Spectrometer (Photon Technology International, South Brunswick, N.J., USA) at excitation wavelengths of 505 and 440 nm and an emission wavelength of 535 nm and converted to the $pH_i$ by means of calibration curves. The cells had already been incubated in $NH_4Cl$ buffer (pH 7.4) in the course of the BCECF loading ($NH_4Cl$ buffer: 115 mM NaCl, 20 mM $NH_4Cl$, 5 mM KCl, 1 mM $CaCl_2$, 1 mM $MgSO_4$, 20 mM Hepes, 5 mM glucose, 1 mg/ml BSA; a pH of 7.4 is established using 1 M NaOH). The intracellular acidification is induced by adding 975 µl of an $NH_4Cl$-free buffer (see below) to 25 µl aliquots of the cells incubated in $NH_4Cl$ buffer. The subsequent rate of the pH recovery was registered at two minutes for NHE1, at five minutes for NHE2 and at three minutes for NHE3. For the calculation of the inhibitory potency of the tested substances, the cells were initially investigated in buffers in which complete or absolutely no pH recovery took place. For complete pH recovery (100%), the cells were incubated in $Na^+$-containing buffer (133.8 mM NaCl, 4.7 mM KCl, 1.25 mM $CaCl_2$, 1.25 mM $MgCl_2$, 0.97 mM $Na_2HPO_4$, 0.23 mM $NaH_2PO_4$, 5 mM Hepes, 5 mM glucose, a pH of 7.0 is established using 1 M NaOH). For the determination of the 0% value, the cells were incubated in an $Na^+$-free buffer (133.8 mM choline chloride, 4.7 mM KCl, 1.25 mM $CaCl_2$, 1.25 mM $MgCl_2$, 0.97 mM $K_2HPO_4$, 0.23 mM $KH_2PO_4$, 5 mM Hepes, 5 mM glucose, a pH of 7.0 is established using 1 M KOH). The substances to be tested were made up in the $Na^+$-containing buffer. The recovery of the intracellular pH at each tested concentration of a substance was expressed in percent of the maximum recovery. The percentages of the pH recovery were used to calculate the $IC_{50}$ value of the particular substance for the individual NHE subtypes by means of the program Sigma-Plot.

Results:

| Example | $IC_{50}$ (NHE3) |
|---|---|
| Example 2 | 0.22 µM |
| Example 5 | 0.15 µM |
| Example 6 | 6.51 µM |
| Example 9 | 1.43 µM |
| Example 10 | 0.32 µM |

The invention claimed is:

1. A compound of the formula I or II

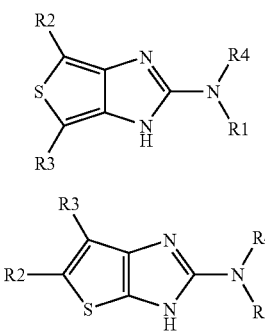

where
R1 is a substituted phenyl of formula:

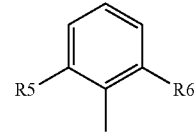

where
R5 and R6 are each independently selected from the group consisting of hydrogen, methyl, ethyl, cycloalkyl having 3, 4 or 5 carbon atoms, vinyl, ethynyl, fluorine, chlorine, bromine, iodine, cyano, trifluoromethyl, $SF_5$, methoxy, nitro and —X—R7;
R7 is alkyl having 1, 2 or 3 carbon atoms, trifluoromethyl or $CH_2$–$CF_3$;
X is $CH_2$, O, NH or $S(O)_n$;
n is zero, one or two;
provided that R5 and R6 are not both hydrogen at the same time;

or
R1 is a substituted 3-thienyl of formula:

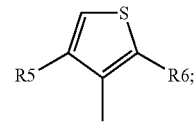

R2 and R3 are each independently selected from the group consisting of hydrogen, fluorine, chlorine, bromine, methyl, CN, OH, —O—$CH_3$, $NO_2$, $NH_2$, —$CF_3$ and —Y—R8;
R8 is methyl, trifluoromethyl or $CH_2$—$CF_3$;

Y is CH$_2$, O, NH or S(O)$_m$;
m is zero, one or two; and
R4 is selected from the group consisting of hydrogen, methyl, ethyl, cyclopropyl, cyclopropylmethyl and CH$_2$—CF$_3$;
or a pharmaceutically acceptable salt or a trifluoroacetic acid salt of a compound of formula I or formula II.

2. A compound of claim 1, which is of formula I, or a pharmaceutically acceptable salt or a trifluoroacetic acid salt of a compound of formula I.

3. A compound of claim 2, wherein:
R5 and R6 are each independently selected from the group consisting of hydrogen, methyl, ethyl, fluorine, chlorine, bromine or trifluoromethyl, provided that R5 and R6 are not both hydrogen at the same time;
R2, R3 and R4 are each hydrogen; or
a pharmaceutically acceptable salt or a trifluoroacetic acid salt of said compound.

4. A compound of claim 2, which is selected from the group consisting of:
2-(4-methyl-3-thienylamino)-1 H-thieno[3,4-d]imidazole,
2-(2,6-dichlorophenylamino)-1 H-thieno[3,4-d]imidazole,
2-(2-trifluoromethylphenylamino)- 1 H-thieno[3,4-d]imidazole,
2-(2,6-dimethylphenylamino)-1 H-thieno[3,4-d]imidazole,
2-(2,6-difluorophenylamino)-1 H-thieno[3,4-d]imidazole,
2-(2-chloro-6-methylphenylamino)-1 H-thieno[3,4-d]imidazole,
2-(2,4-dichloro-3-thienylamino)-1 H-thieno[3,4-d]imidazole, and
2-(2-chloro-4-methyl-3-thienylamino)- 1 H-thieno[3,4-d]imidazole or a pharmaceutically acceptable salt or a trifluoroacetic acid salt of said compound thereof.

5. The compound of claim 4 wherein said salt is a trifluoroacetic acid salt.

6. A compound of claim 4, which is selected from the group consisting of:
2-(2,6-dichlorophenylamino)-1 H-thieno[3,4-d]imidazole,
2-(2-chloro-4-methyl-3-thienylamino)-1 H-thieno[3,4-d]imidazole; and
2-(2,4-dichloro-3-thienylamino)- 1 H-thieno[3,4-d]imidazole or a pharmaceutically acceptable salt or a trifluoroacetic acid salt of said compound thereof.

7. The compound of claim 6 wherein said salt is a trifluoroacetic acid salt.

8. A pharmaceutical composition comprising a compound of claim 1 or a pharmaceutically acceptable salt of said compound together with a pharmaceutically acceptable carrier or additive.

9. A method for the treatment sleep-related respiratory disturbances or sleep apneas which comprises administering to a patient in need thereof an effective amount of a compound of claim 1 or a pharmaceutically acceptable salt thereof.

10. A method for the treatment of snoring which comprises administering to a patient in need thereof an effective amount of a compound of claim 1 or a pharmaceutically acceptable salt thereof.

11. A pharmaceutical composition for human, veterinary or phytoprotective use, comprising an effective amount of a compound of claim 1 or a pharmaceutically acceptable salt of said compound, together with a pharmaceutically acceptable carrier or additive.

12. A pharmaceutical composition of claim 11, further comprising another pharmacological active ingredient or medicament.

13. A process for preparing a compound of claim 1, comprising
a) reacting a diamine of formulae III or IV with a cyanate of the formula V to give a urea derivative of the formula VI or VII; b) cyclizing the urea derivative of the formula VI or VII to give a compound of formulae Ia or IIa; and optionally c) substituting R4 of a compound of formulae Ia or IIa with a non-hydrogen group:

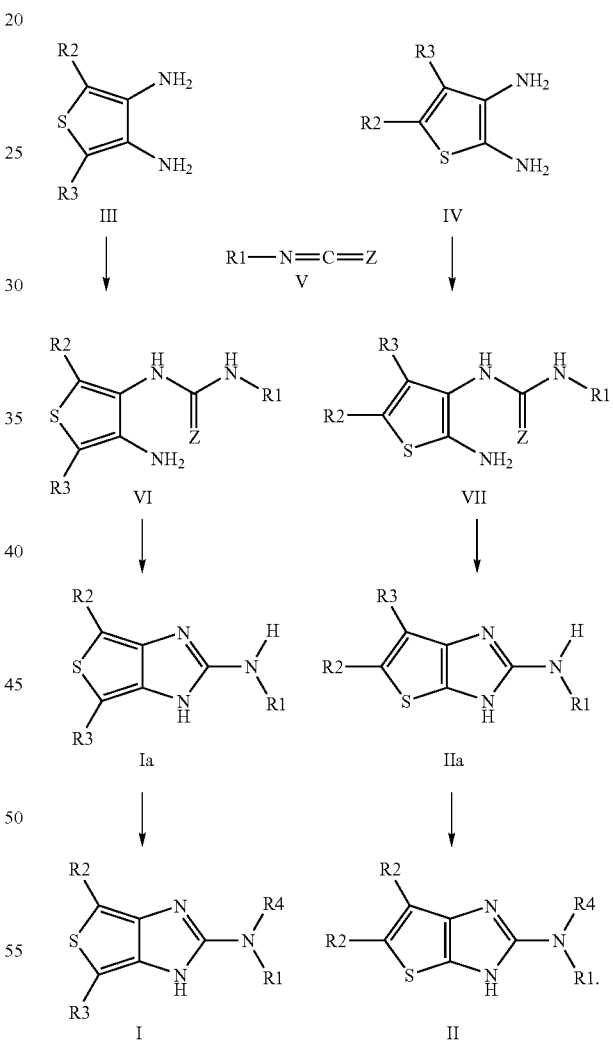

* * * * *